US009095360B2

(12) United States Patent
Chiang et al.

(10) Patent No.: US 9,095,360 B2
(45) Date of Patent: Aug. 4, 2015

(54) FEEDING STRUCTURE FOR DUAL SLOT MICROWAVE ABLATION PROBE

(75) Inventors: Jason Chiang, Madison, WI (US); Christopher Brace, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 554 days.

(21) Appl. No.: 13/441,189

(22) Filed: Apr. 6, 2012

(65) Prior Publication Data
US 2013/0267940 A1 Oct. 10, 2013

(51) Int. Cl.
*A61B 18/18* (2006.01)
*A61B 18/00* (2006.01)

(52) U.S. Cl.
CPC ... *A61B 18/1815* (2013.01); *A61B 2018/00577* (2013.01); *A61B 2018/183* (2013.01); *A61B 2018/1869* (2013.01)

(58) Field of Classification Search
CPC .......... A61B 18/1815; A61B 2018/00023; A61B 18/02; A61B 18/1492; A61B 18/14; A61B 18/18; A61B 2018/1838; A61B 2018/00577; A61N 7/022; A61N 5/04; A61N 1/06

USPC .......................................................... 606/33
See application file for complete search history.

(56) References Cited

U.S. PATENT DOCUMENTS

| 2007/0203551 | A1 | 8/2007 | Cronin et al. |
| 2010/0286687 | A1 | 11/2010 | Feldberg et al. |
| 2011/0034913 | A1 | 2/2011 | Brannan |
| 2011/0060325 | A1 | 3/2011 | Bonn |
| 2011/0208177 | A1 * | 8/2011 | Brannan .......................... 606/33 |

OTHER PUBLICATIONS

Brace, Christopher, Dual-slot antennas for microwave tissue heating: Parametric design analysis and experimental validation, Am. Assoc. Phys. Med., pp. 4232-4240, Med. Phys. 38 (7), Jul. 2011.

\* cited by examiner

*Primary Examiner* — Rex R Holmes
(74) *Attorney, Agent, or Firm* — Boyle Fredrickson, S.C.

(57) ABSTRACT

A dual slot microwave probe for tissue ablation provides axially spaced slots producing an improved heating pattern with reduced axial extent. Degradation in this heating pattern caused by the addition of ceramic support elements and/or fluid cooling is realized through a feeding structure delivering separate sources of microwave energy to the different slots of the probe aligned with the slots of the probe.

19 Claims, 3 Drawing Sheets

FEEDING STRUCTURE FOR DUAL SLOT MICROWAVE ABLATION PROBE

STATEMENT REGARDING FEDERALLY SPONSORED RESEARCH OR DEVELOPMENT

This invention was made with government support under CA142737 awarded by NIH. The government has certain rights in the invention.

CROSS REFERENCE TO RELATED APPLICATION

N/A

BACKGROUND OF THE INVENTION

The present invention relates to microwave probes for tissue ablation and in particular to a microwave antenna providing improved localization of tissue heating.

Microwave and radio frequency ablation may be used to treat tumors, for example in the liver, in patients who are not eligible for surgical removal of the tumor. In microwave ablation, electrical energy with a frequency in the megahertz to gigahertz range is directed into the tumor using a specially designed antenna (ablation probe). The microwave energy received by the tumor and surrounding tissue is converted to heat which destroys tumor cells. Microwave ablation does not require a separate ground pad attached to the patient, and thus may be distinguished from ablation at lower frequencies often termed radiofrequency ablation.

The heat energy deposited into the tissue for a given microwave power and duration may be characterized by the Specific Absorption Rate (SAR) of tissue in the vicinity of the probe. The SAR pattern for a microwave probe may therefore be used to characterize a size and shape of the ablation region. In many applications, the ideal SAR pattern of the microwave probe will be concentrated at the tip of the probe (the portion located in the tumor) and not along the shaft of the probe such as may affect healthy tissue or preclude the use of thermal ablation as a treatment option. Such problems may be reduced, but not eliminated by cooling or insulating the shaft of the probe to decrease thermal conduction between the tissue and the shaft, the latter which may be heated by resistive losses in the transmission of microwave energy. Such thermal conduction provides tissue heating in addition to that produced by radiated microwave energy.

A "dual slot antenna" described in C. Brace, Dual-Slot Antennas for Microwave Tissue Heating Parametric Design Analysis and Experimentation Validation, Med. Phys. 38(7) 4232-4240 (2011), provides an experimental design for a microwave probe providing a distally concentrated SAR at the boundary of the ablation region. Modifying this design by providing thermal cooling of the probe shaft and robust high temperature insulating materials, such as a ceramic antenna support structure, significantly degrades this desirable SAR pattern.

SUMMARY OF THE INVENTION

The present invention provides a dual slot antenna design for a microwave ablation probe having a feeding structure generating the microwaves that are directed through the dual antenna slots. This feeding structure significantly improves the SAR iso-contour of the dual slot antenna when necessary thermal and structural changes are implemented for practical clinical use. In one embodiment, a feeding structure having a localized emission point is used to balance the energy emitted from the dual slots of the antenna.

Specifically, the present invention provides a probe for microwave ablation having a generally elongate shaft extending along a shaft axis and sized for percutaneous insertion into a patient along the axis. The shaft includes an antenna shell having first and second antenna openings for the passage of microwave energy, the first opening being at the distal end of the shaft and the second opening displaced proximally along the axis. A feeding structure is positioned within and spaced from the antenna shell, the feeding structure providing a center conductor connectable to a source of microwave power and a conductive feeding shell surrounding the center conductor and spaced therefrom, the feeding shell having a feeding opening providing a gap between axially displaced sections of the conductive feeding shell for radial passage of microwave energy therethrough.

It is thus a feature of at least one embodiment of the invention to improve the distal concentration of microwave energy in a dual slot microwave antenna offsetting any degradation caused by high temperature ceramic materials and coolant necessary for a practical clinical device.

The feeding opening maybe substantially aligned in a radial direction with the second antenna opening.

It is thus a feature of at least one embodiment of the invention to use the location of the feeding slot to boost the emissions from the proximal antenna slot.

The second antenna and feeding openings have different axial lengths.

It is thus a feature of at least one embodiment of the invention to provide an additional dimension of adjustment for controlling the shape of the radiated field by adjusting the size of the feeding and antenna slots as well as their relative location to the antenna openings.

The first and second antenna openings may be axially flanked by conductive material.

It is thus a feature of at least one embodiment of the invention to control forward projection of the microwave energy by adopting a slot structure at the distal end of the probe.

The probe may include a conductive tip on the distal end of the shaft spaced from the antenna shell and the feeding shell.

It is thus a feature of at least one embodiment of the invention to provide a simple mechanical structure for producing a slot wall for the distal openings.

The distal end of the center conductor may be spaced from the conductive tip.

It is thus a feature of at least one embodiment of the invention to eliminate problems incident to temperature induced stresses that may form in any connection between the center conductor and a metallic tip as caused by high temperature operation of the probe.

The conductive tip may be a sharpened point extending axially.

It is thus a feature of at least one embodiment of the invention to combine the functions of a metallic antenna structure with a forward cutting element facilitating insertion of the probe into tissue.

The antenna shell may be spaced coaxially from the feeding shell to provide a space between portions thereof and a blocking wall may be positioned to extend radially from an outer surface of the feeding shell to an inner surface of the antenna shell, the blocking wall being on a proximal side of the second antenna and feeding openings and defining a compartment sealed at a distal end and open at the proximal end of the shaft for receiving and circulating a cooling fluid.

It is thus a feature of at least one embodiment of the invention to provide active shaft cooling to prevent conductive as well as microwave heating along the shaft extent proximal to the tip of the probe.

The probe may include a coolant tube fitting within the sealed compartment for conducting cooling fluid from the proximal end of the shaft to a point proximate to the blocking wall.

It is thus a feature of at least one embodiment of the invention to provide a simple and compact method of circulating fluid in the full-length of the shaft before the tip of the probe.

The probe may include a cooling fluid of water within the chamber.

It is thus a feature of at least one embodiment of the invention to provide a microwave conductive cooling fluid joining the antenna shell and feeding shell proximal to the second openings.

The probe may include a dielectric material extending radially between portions of the antenna shell and the feeding shell distal to the second antenna and feeding openings.

It is thus a feature of at least one embodiment of the invention to provide a dual slot microwave antenna that is sufficiently rugged for insertion through tissue.

The dielectric material may be a ceramic.

It is thus a feature of at least one embodiment of the invention to provide a dimensionally stable and high temperature material for supporting the antenna shell.

A portion of the dielectric material may extend within the antenna shell proximal to the second antenna opening to provide a blocking impedance to microwave conduction along the antenna shell proximal to the second opening in the antenna shell.

It is thus a feature of at least one embodiment of the invention to employ the supporting dielectric material to block standing wave formation on the shaft of the probe such as may produce resistive heating away from the distal end of the probe.

These particular features and advantages may apply to only some embodiments falling within the claims and thus do not define the scope of the invention.

DETAILED DESCRIPTION OF THE PREFERRED EMBODIMENT

Figure 1:
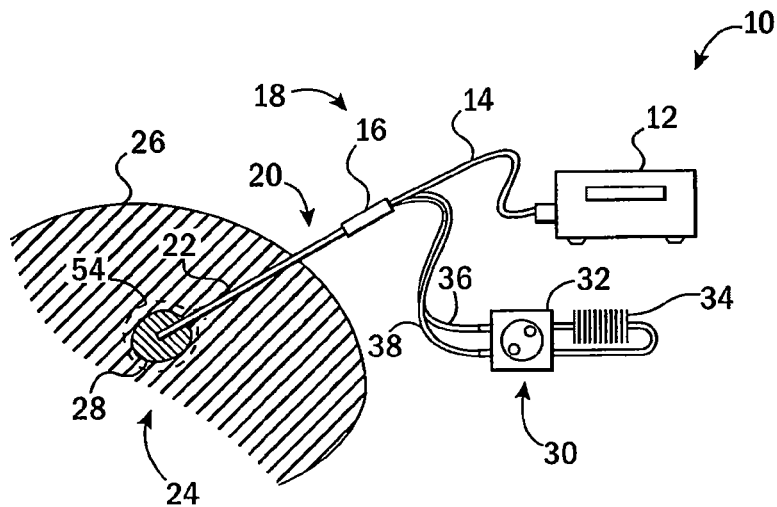
FIG. 1 is a simplified block diagram of a microwave ablation procedure using the probe of the present invention and showing an external microwave source and cooling system with the probe inserted percutaneously into a tumor region.

Referring now to FIG. 1, a microwave ablation system 10 suitable for use with the probe of the present invention may provide a microwave source 12 generating a microwave electrical signal in the microwave region (typically from 1 to 3 GHz), for example at substantially 2.45 GHz for the embodiment described below. A microwave signal from the microwave source 12 may be conducted along a flexible coaxial cable 14 to a connector 16 on a proximal end 18 of a microwave ablation probe 20.

The probe 20 provides a substantially rigid elongate shaft 22 whose distal end 24 may be inserted percutaneously to the skin of the patient 26 so that the distal end 24 lies within a tumor 28. It will be appreciated that the structure of the probe 20 may also be used in open surgery without percutaneous insertion.

An external cooling system 30 may connect with the probe 20 and provide for a pump 32 and heat exchanger 34 communicating via a flexible hose 36 with the connector 16 providing a cooling fluid (such as chilled water or gas) to the probe 20 to cool the shaft 22 of the probe 20 as will be described. A second hose 38 also communicates with the connector 16 to collect exhausted (heated) cooling fluid from the probe 20 for return to the pump 32 to the heat exchanger 34.

Figure 2:
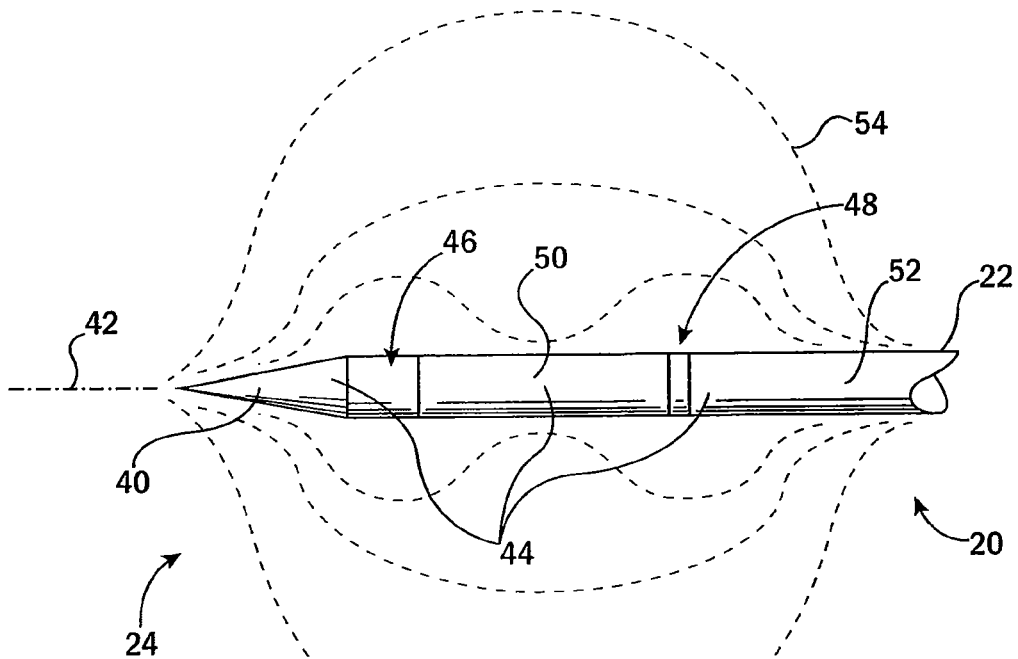
FIG. 2 is a side elevational view of the probe of FIG. 1 showing specific absorption rate iso-contours reflecting a heating pattern provided by the probe.

Referring now to FIG. 2, a distal end 24 of the probe 20 provides a sharpened tip 40 directed along an axis 42 of the shaft 22 permitting insertion of the shaft 22 through tissue. The sharpened tip 40 may be part of a conductive antenna shell 44 extending in a radially symmetric manner about the axis 42 of the probe 20, the conductive antenna shell 44 having a first antenna opening 46 proximate to the sharpened tip 40 and a second antenna opening 48 axially displaced away from the first antenna opening 46 and the sharpened tip 40. Both the first antenna opening 46 and second antenna opening 48 provide circumferential slots in the conductive antenna shell 44 separating the conductive material of the conductive antenna shell 44 into resistively isolated sharpened tip 40, spacer conductive shell 50 (displaced distally and spaced from the sharpened tip 40 by the first antenna opening 46), and shaft shell 52 (displaced distally and spaced from the spacer shell 50 by the second antenna opening 48). Each of the sharpened tip 40, spacer shell 50 and shaft shell 52 may, for example, be constructed of a conductive stainless steel material providing biocompatibility and electrical conductivity.

Microwaves emanating through the first antenna opening 46 and second antenna opening 48 interfere to provide an axially concentrated outer SAR iso-contour 54 defining an ablation region that is axially compressed encompassing a region positioned at the distal end 24. Ideally, a spherical SAR is desired at applicator tip, while axially narrow SAR is desired in preference to an axially elongate SAR for the rest of shaft shell 52, the latter which risks body burning and which does not comport well to typical tumor dimensions.

In one embodiment, an axial length of the first antenna opening 46 may be made approximately 4 mm in axial length, the spacer shell 50 approximately 8 mm in axial length, and the second antenna opening 48 approximately 1 mm in axial length. The diameter of the shaft 22 may, for example, match that of a 17 gauge steel catheter. These dimensions will vary according to the desired shape of the ablation region, the frequency of the microwaves, and other factors including the permittivity of the tissue and are intended simply as guidance and not as a limitation to the invention. Generally antenna opening widths from 1 to 10 mm separated by 1 to 20 mm may be considered and evaluated experimentally or by simulation. Notably, the two antenna openings may be of different axial lengths. Selection and calculation of the proper dimensions for the slots may be determined with reference to the Brace paper cited above and hereby incorporated by reference.

Figure 3:
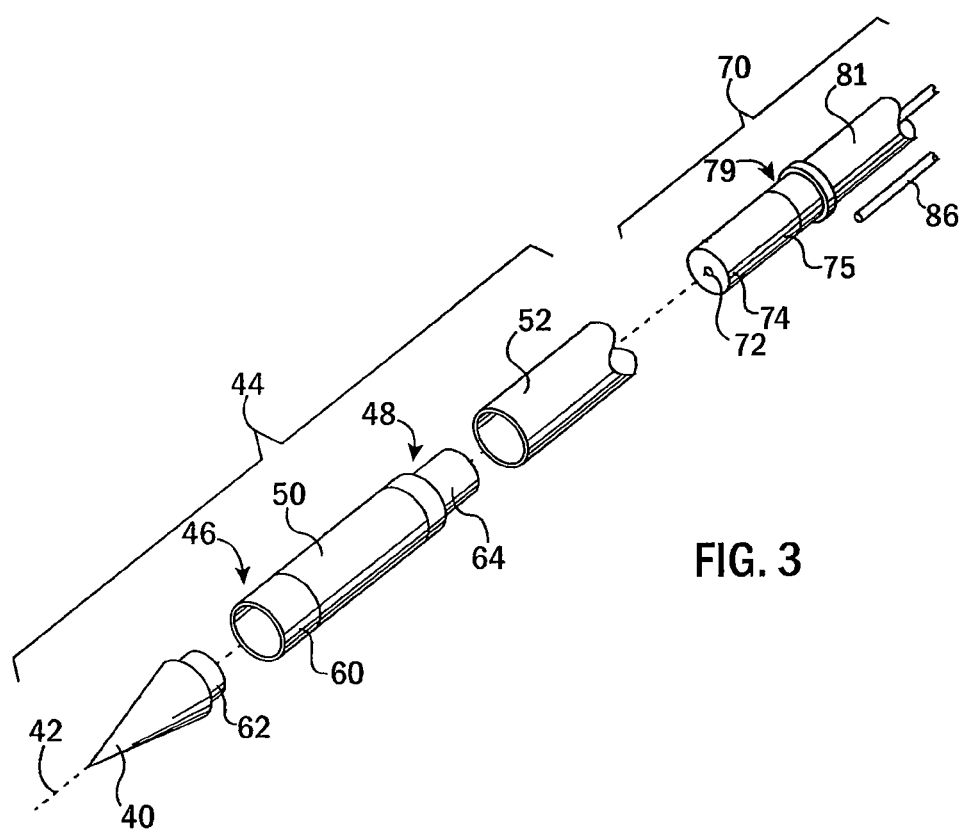
FIG. 3 is an exploded perspective view of the components of the probe showing the formation of two slots in an antenna structure and a central feeding structure.
Figure 4:
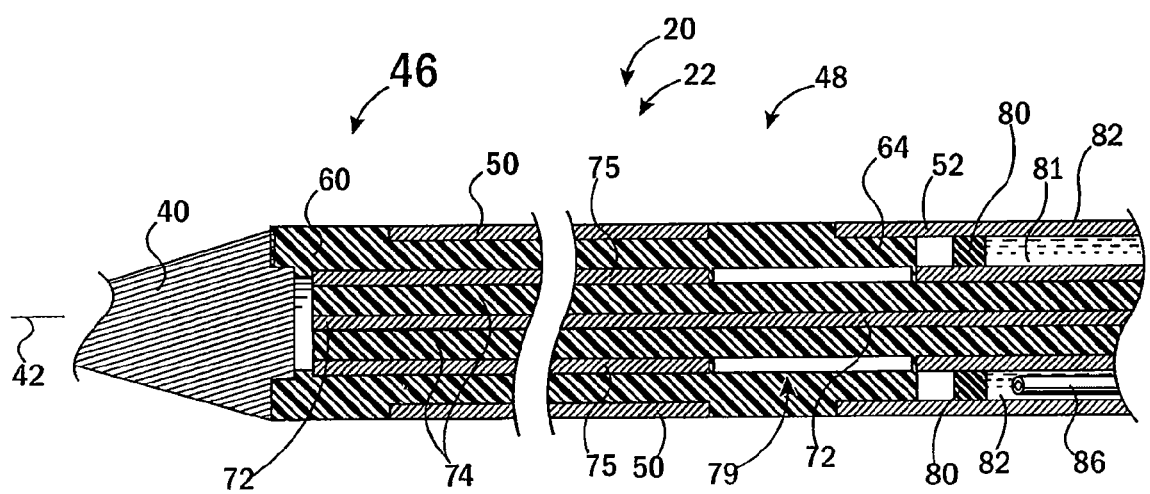
FIG. 4 is a fragmentary side elevational cross-section of the probe of FIG. 3 in an assembled form.

Referring now to FIGS. 3 and 4, the sharpened tip 40, spacer shell 50 and shaft shell 52, together providing the antenna shell 44, form an outermost electrically active component of the probe 20. The spacer shell 50 may be supported on tubular dielectric support 60 receiving at a distal end a cylindrical boss 62 extending from the base of the conical sharpened tip 40 and fitting into the inner diameter of the dielectric support 60 to be retained axially therein. The first antenna opening 46 may be formed by an exposed portion of the dielectric support 60 extending distally beyond the spacer shell 50. Likewise the second antenna opening 48 may be formed by a portion of the dielectric support 60 extending proximally beyond the spacer shell 50 on the opposite side of the spacer shell 50.

A proximal end of the dielectric support 60 may provide a reduced diameter section 64 fitting into the inner diameter of the shaft shell 52 which may, for example, be a standard steel catheter tube having an inner diameter of 0.059 inches. The dielectric support 60 will generally be electrically insulating high temperature material such as a ceramic.

A feeding structure 70 fits within the cylindrical volume defined by the inner wall of the dielectric support 60. The feeding structure 70 generally is formed from a 020-C semi-rigid coaxial cable having a central center conductor 72 surrounded by an insulating dielectric layer 74 (typically polytetrafluoroethylene (PTFE)) with an outer surrounding coaxial conductive spacer shell 75. In a preferred embodiment, the center conductor 72 is spaced from the sharpened tip 40 (for example by a millimeter) providing improved field shaping and eliminating the need for a robust mechanical connection between the conductor 72 and the sharpened tip 40 that might experience high stresses produced by material expansion with heating of the sharpened tip 40 of the probe.

The portion of the feeding structure 70 beneath the spacer shell 50 provides the standard coaxial construction of the center conductor 72 surrounding dielectric layer 74 and outer conductive spacer shell 75.

A feeding opening 79 providing a microwave emission region of the feeding structure 70 is located in a portion of the feeding structure 70 aligned with the second antenna opening 48. The feeding opening 79 is provided by removing the outer conductor of the coaxial cable of the feeding structure in the region beneath the second antenna opening 48 to allow direct broadcasting of microwave energy from the center conductor 72 radially through the feeding opening 79 and out of the second antenna opening 48 and first antenna openings 46.

The remaining length of the feeding structure 70 extending proximally away from the second antenna opening 48 again assumes the standard coaxial cable topology with the center conductor 72, dielectric layer 74, and outer shell 81 providing the coaxial conductive shield.

A blocking wall 80 extends radially from the outer shell 81 of the feeding structure on a proximal side of the second feeding opening 79 to the inner wall of the shaft shell 52 proximal to the opening 48 to define a compartment 82 proximal to the wall 80 that may be filled with a cooling fluid 84 from the cooling system 30 shown in FIG. 1. For this purpose, a small supply tube 86 may be threaded into the compartment 82 to discharge cooling fluid or gas near to the wall 80 which may then flow backward through the compartment 82 to the proximal end of the shaft 22 for extraction therefrom. The cooling fluid 84 may be, for example, water providing an effective conductive short at microwave frequencies between the shell 81 and the shaft shell 52. The blocking wall 80 may, for example, be formed of an insulating material such as epoxy or a conductive material.

Cooling of the shaft shell 52 outside of the ablation region further focuses the ablation toward the distal end of the probe 20 reducing body burns and skin burns. As noted, the feeding structure 70 overcomes the degradation of the ablation pattern when cooling structure and ceramic materials are added to the probe 20.

Figure 5:
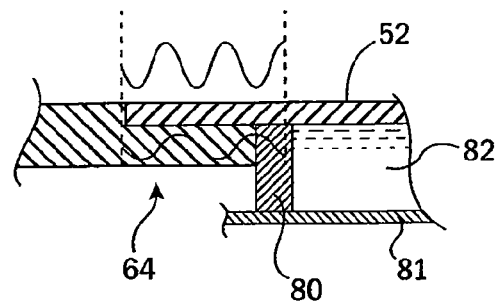
FIG. 5 is a detailed fragment of the cross-section of FIG. 4 showing the formation of a microwave standing wave blocking element from a dielectric spacer supporting a portion of the antenna shell.

Referring now to FIGS. 3, 4 and 5, the reduced diameter section 64 of the dielectric support 60 fitting within the shaft shell 52 may provide an effective high impedance to standing waves forming on the shaft shell 52 which may otherwise create hotspots if not suppressed. Generally, the axial length of the reduced diameter section 64 fitting under the shaft shell 52 may be adjusted to provide a relative phase shift between microwave energy passing directly through the shaft shell 52 from the tip and microwave energy passing through the reduced diameter section 64 from the tip, to provide for destructive cancellation at the desired microwave frequency (for example producing a one half wavelength phase lag). The result is a reduction of standing waves on the shaft shell 52 and thus resistive heating of the shaft shell 52.

The outer surfaces of the probe 20 may optionally be covered by a conformal coating or lubricant material.

Certain terminology is used herein for purposes of reference only, and thus is not intended to be limiting. For example, terms such as "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A probe for microwave ablation comprising:
   a generally elongate shaft extending along a shaft axis and sized for percutaneous insertion into a patient along the axis, the shaft further providing:
   (a) a conductive antenna shell providing a first antenna opening free from conductive material to provide for a radial passage of microwave energy therethrough at a distal end of the shaft and a second antenna opening free from conductive material to provide for a radial passage of microwave energy therethrough, the second antenna opening axially displaced from the first antenna opening toward a proximal end of the shaft; and
   (b) a feeding structure positioned within and spaced from the antenna shell, the feeding structure providing a center conductor connectable to a source of microwave power and a conductive feeding shell surrounding the center conductor and spaced therefrom, the feeding shell having a feeding opening providing a gap free from conductive material between axially displaced sections of the conductive feeding shell for radial passage of microwave energy therethrough.

2. The probe of claim 1 wherein the feeding opening is substantially aligned in a radial direction with the second antenna opening.

3. The probe of claim 1 wherein the second antenna and feeding openings are of different axially extent.

4. The probe of claim 3 wherein the first and second antenna openings are axially flanked by conductive material.

5. The probe of claim 4 further including a conductive tip on the distal end of the shaft spaced from the antenna shell and the feeding shell.

6. The probe of claim 5 wherein a distal end of the center conductor is spaced from the conductive tip.

7. The probe of claim 6 wherein the conductive tip is a sharpened point extending axially.

8. The probe of claim 1 wherein the antenna shell is spaced coaxially from the feeding shell to provide a space between portions thereof and further including a blocking wall extending radially from an outer surface of the feeding shell to an inner surface of the antenna shell, the blocking wall being on a proximal side of the second antenna and feeding openings, the blocking wall defining a compartment sealed at a distal end and open at the proximal end of the shaft for receiving and circulating a cooling fluid.

9. The probe of claim 8 further including a coolant tube fitting within the sealed compartment for conducting cooling fluid from the proximal end of the shaft to a point proximate to the blocking wall.

10. The probe of claim 7 further including a cooling fluid of water within the sealed compartment.

11. The probe of claim 1 wherein a portion of the feeding structure extending distal to the feeding opening has a length providing 180 degrees of phase shift for reflection of the microwave field.

12. The probe of claim 1 further including a dielectric material extending radially between portions of the antenna shell and the feeding shell distal to the second antenna and feeding openings.

13. The probe of claim 12 wherein the dielectric material is a ceramic.

14. The probe of claim 12 wherein a portion of the dielectric material extends within the antenna shell proximal to the second antenna opening to provide a blocking impedance to microwave conduction along the antenna shell proximal to the second opening in the antenna shell.

15. The probe of claim 12 further including a conductive tip supported by the dielectric material axially removed from the antenna shell, the feeding shell, and the center conductor.

16. A method of tissue ablation employing a probe for microwave ablation having:
   a generally elongate shaft extending along a shaft axis and sized for percutaneous insertion into a patient along the axis, the shaft further providing:
   a conductive antenna shell providing a first antenna opening free from conductive material to provide for the radial passage of microwave energy therethrough at a distal end of the shaft and a second antenna opening free from conductive material to provide for the radial passage of microwave energy therethrough, the second antenna opening axially displaced from the first antenna opening toward the proximal end of the shaft;
   a feeding structure positioned within and spaced from the antenna shell, the feeding structure providing a center conductor connectable to a source of microwave power and a conductive feeding shell surrounding the center conductor and spaced therefrom, the feeding shell having a feeding opening providing a gap free from conductive material between axially displaced sections of the conductive feeding shell for radial passage of microwave energy therethrough the method comprising the steps of:
   (a) inserting a distal end of the shaft into tissue to locate the first and second antenna openings in a region to be ablated;
   (b) applying microwave energy between the feeding shell and the center conductor to ablate tissue by microwave energy.

17. The method of claim 16 wherein step (a) inserts the shaft into tissue percutaneously.

18. The method of claim 16 wherein the antenna shell is spaced coaxially from the feeding shell to provide a space between portions thereof and further including a blocking wall extending radially from an outer surface of the feeding shell to an inner surface of the antenna shell, the blocking wall being on a proximal side of the second antenna and feeding openings, the blocking wall defining a compartment sealed at a distal end and open at the proximal end of the shaft for receiving and circulating a cooling fluid; and including the step of circulating a fluid through the compartment.

19. The method of claim 18 wherein the fluid is chilled water.

\* \* \* \* \*